(12) United States Patent
Eklund et al.

(10) Patent No.: US 9,085,519 B2
(45) Date of Patent: Jul. 21, 2015

(54) PROCESSES FOR PRODUCING BENZOPHENONE DERIVATIVES

(75) Inventors: Lars Eklund, Karlskoga (SE); Jonas Nilsson, Karlskoga (SE)

(73) Assignee: Cambrex Karlskoga AB, Karlskoga (SE)

( * ) Notice: Subject to any disclaimer, the term of this patent is extended or adjusted under 35 U.S.C. 154(b) by 412 days.

(21) Appl. No.: 13/521,910

(22) PCT Filed: Jan. 19, 2011

(86) PCT No.: PCT/GB2011/000058
§ 371 (c)(1),
(2), (4) Date: Oct. 12, 2012

(87) PCT Pub. No.: WO2011/089385
PCT Pub. Date: Jul. 28, 2011

(65) Prior Publication Data
US 2013/0035514 A1    Feb. 7, 2013

Related U.S. Application Data

(60) Provisional application No. 61/296,096, filed on Jan. 19, 2010.

(51) Int. Cl.
  *C07C 41/30* (2006.01)
  *C07C 41/34* (2006.01)
  *C07C 45/72* (2006.01)

(52) U.S. Cl.
  CPC .............. *C07C 41/30* (2013.01); *C07C 45/72* (2013.01)

(58) Field of Classification Search
  USPC ................................................ 568/641, 640
  See application file for complete search history.

(56) References Cited

U.S. PATENT DOCUMENTS

| 2,182,786 A | 12/1939 | Coleman et al. |
| 2,831,768 A | 4/1958 | Merrill et al. |
| 4,625,048 A | 11/1986 | Zurfluh |
| 4,885,396 A * | 12/1989 | Hahn et al. ............. 568/315 |
| 4,996,225 A | 2/1991 | Toivola et al. |
| 5,118,859 A | 6/1992 | Aumueller et al. |
| 5,750,576 A | 5/1998 | DeGregorio et al. |
| 6,576,645 B1 | 6/2003 | Sodervall et al. |
| 2008/0207956 A1 | 8/2008 | Sodervall et al. |
| 2008/0214860 A1 | 9/2008 | Sodervall et al. |

FOREIGN PATENT DOCUMENTS

| CS | 196471 | 3/1980 |
| EP | 0072475 | 2/1983 |
| EP | 0425974 | 5/1991 |
| WO | 9607402 | 3/1996 |
| WO | 9942427 | 8/1999 |
| WO | 0160775 | 8/2001 |

OTHER PUBLICATIONS

Duan et al., "Insights into the General and Efficient Cross McMurry Reactions between Ketones," J. Org. Chem. 2006, 71, 9873-9876.
International Search Report and Written Opinion for PCT/GB2011/000058 dated Apr. 21, 2011.
Duan et al: J. Org. Chem., vol. 71, 2006, pp. 9873-9876, XP002632185, tables 1 entries 16, 17 compounds 1a, 1n, 2an,1o, 2ao p. 9874, col. 1, paragragh 2.
International Preliminary Report and Written Opinion for PCT/GB2011/000058 dated Jul. 24, 2012.

* cited by examiner

*Primary Examiner* — Rosalynd Keys
(74) *Attorney, Agent, or Firm* — Banner & Witcoff, Ltd.

(57) ABSTRACT

There is provided a process for the preparation of a compound of formula I,

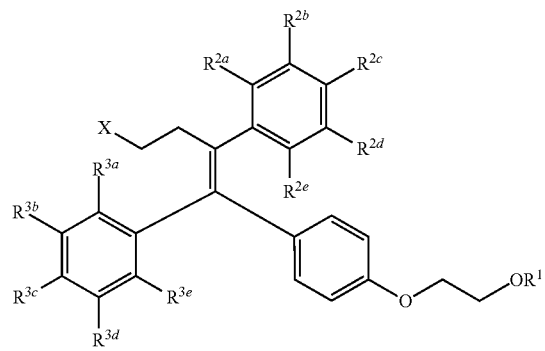

wherein X, $R^1$, $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ are as described in the description. Such compounds may, for example, be useful medicament (or intermediates for medicaments).

21 Claims, No Drawings

PROCESSES FOR PRODUCING BENZOPHENONE DERIVATIVES

This application claims priority to International Patent Application No. PCT/GB2011/000058, filed Jan. 19, 2011 and claims the benefit of U.S. Provisional App. No. 61/296,096, filed Jan. 19, 2010, both of which are incorporated herein by reference in their entirety.

The present invention relates to a process for the manufacture of certain benzophenones, and derivatives thereof, which may be useful intermediates in the synthesis of further compounds, especially drugs (e.g. containing alkenes), for instance estrogen receptor modulators such as Ospemifene® (also known as Ophena® or Z-2-[4-(4-chloro-1,2-diphenyl-but-1-enyl)phenoxy]ethanol).

International patent applications WO 99/42427 and WO 96/07402 describe the synthesis of certain derivatised tetra-substituted alkenes, the former describing the preparation of E-2-[4-(4-chloro-1,2-diphenyl-but-1-enyl)phenoxy]ethanol, wherein the synthesis starts from a tetra-substituted alkene precursor E-4-(4-hydroxy-1,2-diphenyl-but-1-enyl)-phenol. There is no disclosure in either document of any tetra-substituted alkene forming reaction. However, in a referenced document, U.S. Pat. No. 4,996,225, there is described the formation of a tetra-substituted alkene by an elimination reaction of a 2,2,3-tri-substituted tetrahydrofuran.

In the general field of organic chemistry, the McMurry reaction is known, and comprises a coupling reaction of two compounds, each containing carbonyl moieties, to form an alkene (which may be tetra-substituted). The reaction is a reductive coupling that requires the use of a titanium chloride and a reducing agent, and can be known to be limited in scope and versatility.

The McMurry reaction may use a benzophenone starting material, of which several are known and commercially available. Certain other substituted/derivatised benzophenones may need to be prepared.

European patent application EP 0 072 475 discloses (see e.g. Example 4) the synthesis of various benzophenone compounds, including 4-(2-hydroxyethoxy)benzophenone, from the alkylation of 4-hydroxybenzophenone with ethylene carbonate. Such a reaction is performed in the presence of tetrabutylammonium bromide (as a catalyst), in which the reaction in the presence of dimethylformamide as a solvent, under dilute reaction conditions.

Czech patent CS 196471 discloses the synthesis of a certain benzophenone, which comprises the Friedel-Crafts acylation onto the benzene ring of a 1-carboxy-2-phenoxy-ethane. There is no disclosure in this document of the alkylation of a hydroxy moiety, which latter moiety is pended to an already-formed benzophenone.

U.S. Pat. No. 2,831,768 and U.S. Pat. No. 2,182,786 each describe the preparation of 4-(2-hydroxyethoxy)benzophenone by the alkylation of 4-hydroxybenzophenone with ethylene chlorohydrin (2-chloroethanol), which reactions take place in the presence of aqueous sodium hydroxide or aqueous ethanolic sodium hydroxide. There is no disclosure of a corresponding reaction with a different alkylating agent.

International patent application WO 01/60775 describes an alkylation reaction using ethylene carbonate and a catalyst, such as a metal halide. However, this document does not disclose a corresponding reaction on a 4-hydroxybenzophenone. Furthermore, it concerns sequential reactions, where a 2-hydroxyethoxy side chain that is introduced is further alkylated at the free hydroxy site.

Finally, European patent application EP 0 425 974 and U.S. Pat. No. 5,118,859 disclose an alkylation of a certain hydroxy moiety, using ethylene carbonate.

The listing or discussion of an apparently prior-published document in this specification should not necessarily be taken as an acknowledgement that the document is part of the state of the art or common general knowledge.

In a first aspect of the invention, there is provided a process for the preparation of a compound of formula I,

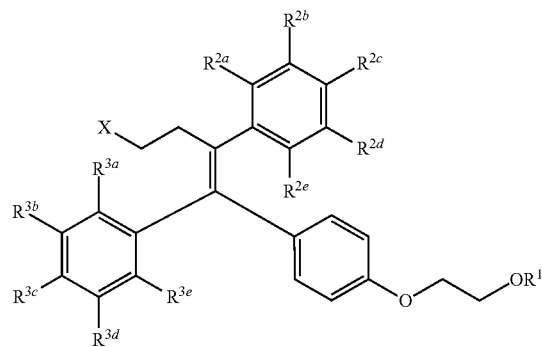

wherein:
X represents halo or —OH;
$R^1$ represents H or $C_{1-6}$ alkyl optionally substituted by one or more —OH group;
each $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ independently represent H or —OH;
which process comprises reaction of a compound of formula II,

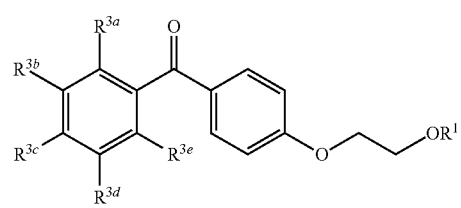

wherein $R^1$ and $R^{3a}$, $R^{3b}$, $R^{3c}$, $R^{3d}$ and $R^{3e}$ are as defined above, with a compound of formula III,

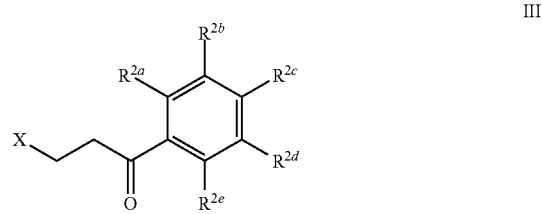

wherein X and $R^{2a}$, $R^{2b}$, $R^{2c}$, $R^{2d}$ and $R^{2e}$ are as defined above,
which process is hereinafter referred to as "the process of the invention". Further, compounds of formula I prepared by the process of the invention may be referred to hereinafter as the compounds of the invention.

The process of the invention may be performed employing salts, solvates or protected derivatives of the compounds of formulae II and III. Compounds of formula I that may thereby be produced may or may not be produced in the form of a (e.g. corresponding) salt or solvate, or a protected derivative thereof. In a further embodiment of the invention, if the compound of formula I is obtained in a form that is not a salt, it may be converted into an appropriate (e.g. pharmaceutically acceptable) salt, if desired.

The compounds employed in or produced by the processes described herein may contain double bonds and may thus exist as E (entgegen) and Z (zusammen) geometric isomers about each individual double bond. All such isomers and mixtures thereof are included within the scope of the invention. Hence the compound of formula I that may be formed may exist as either the E-isomer, Z-isomer or as a mixture of such geometric isomers.

It is stated herein that the compound of formula I that may be produced by the process of the invention can exist as either the E or Z geometric isomer. However, it is preferred that the Z-isomer is the isomer that is predominantly produced, and hence why the compound of formula I is depicted graphically as the Z-isomer. Preferably, the process of the invention provides compounds of formula I in which the ratio of Z:E isomers is greater than 1:1 (for instance, greater than, or about, 2:1, preferably greater than, or about, 3:1 and, more preferably, greater than, or about, 4:1 (e.g. about 4.3:1)). Advantageously, in an embodiment of the invention, the ratio may be greater than 5:1, for instance about 5.5:1. In a further embodiment of the invention, the process of the invention may allow even better selectivities (of Z:E) to be achieved, for instance if the compound of formula I is obtained in crystalline form, then crystallisation/recrystallisation techniques may be employed (such as those described herein). In such instances, the product of formula I may be obtained in Z:E ratios of greater than 10:1, e.g. the Z-isomer may be obtainable in a ratio of about or greater than 95% (compared to the E-isomer), e.g. >98% such as about or >99% and most preferably there is substantially only Z-isomer (e.g. about 100%) and no (or an insignificant amount of) E-isomer.

In the process of the invention, preferred compounds of formula I that may be produced include those in which:
X represents halo (most preferably, chloro); and/or
$R^1$ represents H.

In the process of the invention, further preferred compounds of formula I that may be produced include those in which:
when $R^1$ represents optionally substituted $C_{1-6}$ alkyl, then it is preferably substituted by one —OH group (e.g. at the terminal position of the alkyl group, so forming e.g. a —$CH_2$—$CH_2$—OH moiety);
at least three (e.g. at least four) of $R^{2a}$ to $R^{2e}$ represent(s) hydrogen (and the other(s) represent —OH or H); or, most preferably,
$R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ all represent hydrogen.

The process of the invention is preferably performed in the presence of a solvent (or mixture of solvents). The type of solvent may be any that is suitable for the McMurry reaction, for instance an aromatic solvent (e.g. toluene, or the like) or, preferably, a polar aprotic solvent (such as diethyl ether, tetrahydrofuran or dimethoxyethane), or a mixture of any of these solvents. Other solvent systems that may be mentioned include other ethereal solvents, such as dioxane, diglyme, dibutylether, methyl-tert-butyl ether (or mixtures thereof), or a mixture of solvents such as pyridine and tetrahydrofuran, toluene and tetrahydrofuran, and 2-methyltetrahydrofuran and toluene. However, advantageously, the process of the invention is performed in the presence of an ethereal solvent, which surprisingly leads to an unexpected increase in yield (especially when performed in the presence of 2-methyltetrahydrofuran) and therefore also makes it possible to isolate the desired compound of formula I by crystallisation (isolation of the compound of formula I by crystallisation may not be possible if the yield is low, and/or the crystallisation solvent is not suitable).

When solvent is employed, then preferably between about 0.1 mL and about 10 mL of the total amount of solvent per mmol of compound of formula II (or compound of formula III) is employed, for instance between about 0.2 mL and 8 mL per mmol, and preferably between about 0.5 mL and 5 mL (e.g. about 3.5 mL or preferably about 2.5 mL per mmol of compound of formula II (or compound of formula III)). The amount of solvent employed (i.e. the concentration of the compounds of formulae II and III in the process of the invention) may have an effect on the yield and/or selectivity of the process of the invention. For instance, when the reaction mixture is more dilute, advantageously the yield and/or selectivity (Z:E) of the process of the invention may increase. Hence, in an embodiment, the process of the invention advantageously proceeds in the presence of up to, or about, 10 mL solvent (e.g. up to, or about, 5 mL such as about 3.5 mL) per mmol of compound of formula II. On the other hand, clearly, for environmental reasons, minimising the volume of solvent employed should also be a consideration. Hence, typically, about 3.5 mL (e.g. 3.7 mL) of solvent per mmol of compound of formula II (or compound of formula III) is employed. However, the exact quantity of solvent does not have a large bearing on the process of the invention (or on the essence of the invention). It will be appreciated by the skilled person that fundamentally the process of the invention may be performed at any suitable concentration.

The process of the invention comprises the McMurry reaction between the (carbonyl moieties of) compounds of formulae II and III. The reaction is therefore performed in the presence of a titanium chloride compound, for instance $TiCl_3$ or preferably, $TiCl_4$, and in the presence of a reducing agent (or, employing other suitable reducing methods or conditions; preferably, it is in the presence of a reducing agent), for instance, $LiAlH_4$ (or the like, e.g. $Al/AlCl_3$), or a reducing metal such as aluminium, potassium, magnesium or preferably zinc, such as zinc dust/powder (others that may be mentioned include Zn—Cu couple, lithium, sodium, calcium and Mg/Hg). The most preferred combination includes $TiCl_4$ and zinc (e.g. zinc dust). Other reducing methods/conditions that may be mentioned include the presence of another suitable reducing metal that may be more environmentally-friendly than those mentioned above (e.g. zinc), such as magnesium, calcium or certain other group I or group II metals.

Typically, the molar ratio of the compounds of formula II and III in the process of the invention is about 1:1 (but may be anywhere between about 2:1 and 1:2, and may depend on which material the skilled person wants to use in excess).

Preferably, at least one molar equivalent of the titanium chloride compound (e.g. $TiCl_4$) is employed and, more preferably, it is used in excess, e.g. in a ratio of about (or greater than) 1.1:1 of titanium chloride compound and compound of formula II (or III), preferably, about (or greater than) 1.2:1 and most preferably about (or greater than) 1.3:1 (e.g. about 1.35:1). Other preferred quantities of the titanium chloride that may be mentioned include about (or greater than) 1.5:1 for instance between 1.5:1 and 3:1, such as about 1.75:1 to 2.25:1, e.g. about 2:1).

The amount of reducing agent should be at least sufficient (in molar equivalent terms) to enable the reduction to take place fully. As stated hereinbefore, the reducing agent that is present may be a reducing metal, such as zinc (e.g. zinc dust/powder). When it is a reducing metal, then the number of equivalents depends upon the number of electrons that are required to be gained by the reaction (i.e. the process of the invention). For instance, when the reducing metal is zinc, there is preferably at least two molar equivalents present compared to the compound of formula II (or the compound of formula III) employed in the process of the invention, for instance about (or at least) 2 equivalents, preferably about (or at least) 2.5 equivalents. Preferably, the number of equivalents of reducing metal (e.g. when it is zinc) compared to the compound of formula II (or the compound of formula III) is between about 2 and 5 equivalents (e.g. between about 2.5 and 4 equivalents, such as at least, or about, 3.5 equivs, such as about 3.8 equivalents). Typically, however, the number of equivalents of the reducing metal (e.g. zinc) in the process of the invention is compared to equivalents of titanium compound employed. As such, there is preferably at least one equivalent of reducing metal (e.g. zinc) per equivalent of titanium compound, but preferably at least, or about, 1.5 equivalents of reducing metal per equivalent of titanium compound, e.g. between about 1.5 and 2.5 equivalents, such as between about 1.7 and 2.3 equivalent), especially about 2 equivalents.

The reagents/starting materials, and any solvent that may be present, may be added to the reaction vessel in any order. For instance, the reducing agent (e.g. zinc dust) may be first added to the reaction vessel, together with any (e.g. a portion of) solvent (e.g. 2-methyltetrahydrofuran) that may be employed. Then, the mixture of reducing agent and solvent may or may not be (i.e. the mixture may be maintained at the same temperature) cooled to below room temperature, for instance below about 10° C., e.g. below about 0° C., and preferably cooled to about −5° C. The titanium chloride compound (e.g. $TiCl_4$) may then be added to the reaction mixture, and this addition is preferably slow as the addition is exothermic. The addition will depend on the quantity of titanium chloride compound and the overall scale of the reaction. However, when about 10 mmol of titanium chloride compound is employed, then the addition may be over a period of at least 5 minutes, preferably, at least 10 minutes, and more preferably, over about 20 minutes. In any event the addition of the titanium chloride compound is at such a rate as to preferably maintain the overall reaction temperature below, or about, 25° C., for instance below, or about, 10° C. (preferably below about 0° C.). After the addition of the titanium chloride compound, the reaction mixture (i.e. mixture of solvent, reducing agent and titanium chloride compound) may then be heated to a suitable temperature (e.g. to above 30° C., for example above 50° C., preferably, above 80° C. and most preferably at about 80 to 82° C., or, at reflux), for instance for at least one hour, e.g. about 2 hours. To this reaction mixture, the compounds of formulae II and III may then be added (i.e. at the elevated temperature range indicated above, most preferably at reflux). This 'complete' reaction mixture may then be heated at the elevated temperatures set out above (e.g. at reflux) for a further period of time, e.g. at least one hour, e.g. about 2 hours. The skilled person may be able to determine (and/or adjust) the length of the reaction.

It is stated above that the reagents/starting materials/solvent may be added in any order. In an embodiment of the invention, the compounds of formulae II and III, the reducing agent (e.g. reducing metal, such as zinc) and solvent (e.g. 2-methyltetrahydrofuran) may be added to the reaction vessel first. Preferably, this initial mixture (which may be a slurry) is de-gassed and the vessel filled with an inert gas (e.g. nitrogen). The process of the invention proceeds in a more efficient manner when performed under an inert atmosphere (thereby providing better yields, more pure products, etc). The reaction mixture may be cooled to below room temperature as described herein, for instance it may be cooled to at or below 15° C. before the addition of the titanium compound (e.g. $TiCl_3$ or preferably $TiCl_4$). As mentioned hereinbefore the titanium compound is preferably added to the reaction mixture such that the reaction temperature is maintained below about 20° C., hence the compound may be added slowly over a period of time. The reaction mixture (compounds of formula II and III, reducing agent, titanium compound and solvent) may then be heated to above room temperature, for instance to above about 40° C., e.g. about 50° C., and the reaction mixture may be held at that temperature for a period of time (e.g. between about 5 and 25 minutes, such as about 15 minutes). Thereafter, solvent (e.g. 2-methyltetrahydrofuran) that may be present in the reaction mixture may be distilled therefrom (preferably more than 10% of the solvent, e.g. more than 25%, such as more than, or about, 50%, e.g. about 55% of the solvent is distilled off), for instance by heating the reaction mixture (e.g. at about 70° C.) under reduced pressure (e.g. at about 650 mbar) for a period of time (e.g. over about 1 hour), depending on the time taken for the desired amount of solvent to be removed. The reducing agent (e.g. reducing metal, such as zinc) may then be removed (e.g. by filtration) and further solvent (e.g. 2-methyltetrahydrofuran, up to 100% of that remaining) may be removed by distillation. Advantageously, the solvent that may be employed in the process of the invention may be recycled in this manner (e.g. more than 50% may be recycled such as about 75%, but even up to substantially all of the solvent employed may be recycled). Clearly, this has a beneficial advantage, e.g. from an environmental and cost point of view.

Advantageously, the reaction need not be complete before the distillation of the solvent (e.g. 2-methyltetrahyrofuran) that may be employed in the process of the invention (e.g. at the point when the reaction mixture is heated to above room temperature and held for a period of time). For instance, at this point the reaction mixture may consist of intermediate product(s) such as one or more alcohol or diols. However, the reaction of the process of the invention may proceed to completion (or to higher yields) at the same time as any solvent (e.g. 2-methyltetrahydrofuran) is distilled from the reaction mixture (for instance as described hereinbefore). This is advantageous as the reaction of the process of the invention is combined with the removal (by distillation; recycling) of the solvent (e.g. 2-methyltetrahydrofuran), therefore increasing the efficiency of the process.

It is stated above that the compounds of formulae II and III may be added to the reaction mixture (i.e. to the reaction vessel containing the reducing agent), in which case the compounds of formulae II and III may themselves be pre-dissolved in a portion of the solvent that may be employed in the process of the invention. However, the compounds of formulae II and III may be in batches (i.e. in any proportions/order, wherein a 'batch' may be a proportion of only compound of formula II, only compound of formula III or a mixture of compounds of formulae II and III, in which each batch of compound/compounds may be dissolved or pre-dissolved in the solvent employed in the process of the invention). Hence, the addition may be as follows: addition of 10% of the compound of formula II (or the compound of formula III), followed by addition of a mixture containing the remaining 90% of the compound of formula II (or III) and (100% of) the compound of formula III (or II, as appropriate). The foregoing example is merely illustrative of possible batch-wise, or 'shifted', addition of the reagents of the process of the invention. Additionally, the addition need not be of the compounds of formulae II and III to the reaction vessel containing the reducing agent, the order of addition may be such that the reducing agent (e.g. the combination of $TiCl_4$ and zinc; optionally in the presence of solvent that may be employed in the process of the invention, e.g. 2-methyltetrahydrofuran) is added to the compounds of formulae II and III (which compounds may be pre-dissolved in a solvent employed in the process of the invention, e.g. 2-methyltetrahydrofuran). After the addition of all of the reagents that are employed in the process of the invention, as stated above, the 'complete' reaction mixture may then be heated at reflux (or at the elevated temperature range indicated hereinbefore) for a further period of time, e.g. at least one hour, e.g. about 2 hours (although the actual length of time may be determined by the skilled person).

After the 'complete' reaction mixture is heated at the elevated temperature range indicated hereinbefore (e.g. at reflux), it may then be cooled to about room temperature, after which aqueous acid (e.g. an aqueous hydrohalide such as aq. HCl) may be added in order to quench the reaction. The aqueous acid may be added in portions in order to minimise the heat produced, for instance a portion of 1 M HCl may be added, and then a further portion of 6 M HCl may be added. The desired compound may then be extracted with a suitable organic solvent, e.g. an aromatic solvent such as toluene, or, further solvent need not be added in the extraction step, for example if the reaction mixture is biphasic after it is quenched (in which case the phases may be separated).

For instance, after the solvent employed in the process of the invention (e.g. 2-methyltetrahydrofuran) is distilled off from the reaction mixture, solvent (e.g. an aromatic organic solvent such as toluene) may be added before the reaction is quenched as indicated above, preferably maintaining the reaction mixture below about 20° C. (hence adding the quenching reagent, e.g. aqueous HCl in portions). The desired product (in the organic layer) may then be separated (or "cut") from the aqueous layer (e.g. at elevated temperature, e.g. at about 30° C.), and the organic layer may then be washed (for instance with two portions of water, which may subsequently be cut and discarded at elevated temperature, e.g. at about 55° C.). The organic layer (which may comprise solvent employed in the process of the invention, e.g. toluene and residual 2-methyltetrahydrofuran and water) may then be concentrated, for instance by distillation under reduced pressure (e.g. at between about 37° C. to 60° C. at about 150 to about 50 mmbar) to leave residual solvent. To the residual solvent, a solvent system that promotes crystallisation is added (e.g. methanol and water, as described hereinafter). Such a process may advantageously increase yield, purity and/or selectivity of the desired compound of formula I.

The elevated temperatures employed in the work-up procedures are not essential, as the organic and aqueous phases may be cut/separated at room temperature, however, although it is not critical, it is preferred that elevated temperatures (such as the ones mentioned hereinbefore) are employed in order to achieve faster phase separation, thereby increasing the efficiency of the work-up procedure. This may be particularly important when a scaled-up process is employed.

Given the nature of the process of the invention and the reagents employed, the process of the invention is preferably performed in the presence of an inert atmosphere, e.g. under a nitrogen atmosphere.

It is stated above that crystallisation of the compound of formula I may be effected in a certain solvent. Hence, in a further aspect of the invention, there is provided a process for the isolation/purification of a compound of formula I, as hereinbefore defined, which process comprises crystallisation or precipitation of the compound, in a solvent system, which is hereinafter also referred to as a process of the invention.

The solvent system may comprise an alcohol (e.g. methanol), optionally mixed with water. The compound of formula I may first be dissolved in the solvent system (and optionally heated, in order to achieve dissolution and/or to obtain a clear solution), and then cooled to room temperature (or below, e.g. at or below 25° C., such as at or below 20° C., preferably at or below 15° C., and more preferably at or below 10° C., e.g. at about 8° C.) in order to achieve the crystallisation. The solvent system preferably comprises a mixture of alcohol and water. The solvent system may also comprise a mixture of acetone and water, ethyl acetate and heptanes and/or toluene and heptanes. It is preferred that one of the solvents of the solvent system (which is preferably a mixture of two or more (e.g. two) different solvents) comprises a relatively polar solvent such as water, an alcohol (e.g. methanol or isopropanol), dimethylformamide, acetic acid and/or propionic acid. For instance, the solvent system comprises at least 10% of such a mixture (e.g. a mixture of alcohol and water), for instance, at least 25% and preferably at least 50%. More preferably, the solvent system comprises at least 75% of such a mixture, particularly at least 90%, e.g. at least 95%, and most preferably the solvent system comprises exclusively a mixture of alcohol and water (i.e. at, or near, about 100%; the solvent system possibly comprising less than 5% (preferably less than 2%, e.g. less than 1%) of other solvents and/or impurities).

When a mixture of an alcohol (e.g. methanol) and water are used as the solvent system, then preferably the alcohol is present as the major solvent, i.e. the ratio (by volume) of alcohol:water is greater than 1:1, for instance, greater than 2:1, e.g. about or greater than 3:1 (e.g. 4:1) and most preferably about, or greater than, 5:1 (e.g. about 5.2:1). The volume of solvent (e.g. methanol and water mixture, or 2-methyltetrahydrofuran) may be determined by the skilled person, depending on the quantity of material to be crystallised. However, it is preferred that, when quantitative reaction (between compounds of formulae II and III) is assumed, then the volume of crystallisation solvent is most preferably about 2 mL per mmol of compound of formula I (that is assumed to be produced by a quantitative reaction), although any suitable volume of solvent is adequate, for instance between 0.5 mL per mmol and 10 mL per mmol (e.g. between 1 mL per mmol and 5 mL per mmol). In order to increase purity of the desired compound of formula I, the volume of solvent (per mole of compound of formula I) in the crystallisation/precipitation process may be relatively high.

The crystallisation/precipitation process of the invention described herein has the additional advantage that the compound of formula I may be present in the reaction mixture with other products (e.g. unreacted starting material or other undesired side-products), but this purification/isolation process may still proceed. For example, the compound of formula I may be present in less than 95% (e.g. less than 90%, such as less than 80%; or even less than 50%, e.g. less than, or about 40%, the remainder being by-products) of the mixture to be crystallised/precipitated, but the isolated/purified product so formed may not contain those undesired products (and may be present in a higher percentage, such as above 95%, e.g. above 99%, such as near, or at, 100%, in the product formed).

Further, the crystallisation/precipitation process of the invention may also increase the Z:E selectivity of the compound of formula I produced by the process of the invention. Hence, not only may the crystallisation/precipitation process isolate the product of formula I from unreacted starting material or other undesired products, it may improve the Z:E ratio. As stated hereinbefore, the ratio is greater than 1:1, for instance greater than, or about, 4:1. The crystallisation/precipitation process of the invention may increase this ratio to about, or greater than, 10:1, for instance about, or greater than 20:1 (e.g. 50:1), and especially about, or greater than 90:1 (e.g. 99:1) e.g. in particular in which the product obtained comprises substantially all (e.g. 100%, or thereabouts) Z-isomer. Clearly, the fact that the process of the invention provides a crystallisable product is advantageous as the Z-isomer of the product is obtainable and can then be isolated.

In the crystallisation/isolation process of the invention, the solvent system (which comprises e.g. methanol, water and residual toluene) in which the compound prepared by the process of the invention is dissolved may be heated to e.g. about 50° C., then cooled to about 48° C. and optionally (and preferably) seeded. The mixture may then be cooled over a period of time (e.g. slowly, e.g. over more than one hour, such as over about 5 hours) to at or below room temperature (e.g. to about 15° C.), after which this temperature may be maintained for a further period of time (e.g. more than 2 hours, such as more than 6 hours, e.g. more than or about 12 hours) depending on the quantity of product that is crystallised/precipitated out of solution (i.e. the period of time may be more or less; yield may be increased if the period of time is longer). The product may thereafter be separated/isolated, e.g. by filtration. Such a process may advantageously increase yield, purity and/or selectivity of the desired compound of formula I. For instance a compound of formula I in increased purity and/or in better selectivity (i.e. better ZE selectivity as indicated above) may be obtained. Further, recrystallisations (e.g. performed in the crystallisation solvent systems described herein) may also further increase purity/selectivity, etc.

The crystallisation/recrystallisation processes of the invention allows high purities to be achieved, for instance HPLC purities of greater than 90%, e.g. greater than 95%, such as greater than 98% (e.g. greater than 99%, such as greater than 99.5% or 99.9%).

Crystallisation temperatures and crystallisation times depend upon the concentration of the compound in solution, and upon the solvent system which is used.

The formation of a particular crystalline form of a compound may be advantageous (as compared to, for example, an amorphous form), as crystalline forms may be easier to purify and/or handle. Crystalline forms may also have a better solid state stability and shelf-life (e.g. be stored for longer periods of time without substantial change to the physico-chemical characteristics, e.g. chemical composition, density and solubility).

The skilled person will appreciate that, if a compound can be obtained in stable crystalline form, then several of the above-mentioned disadvantages/problems with amorphous forms may be overcome. It should be noted that obtaining crystalline forms is not always achievable, or not easily achievable. Indeed, it is typically not possible to predict (e.g. from the molecular structure of a compound), what the crystallisation behaviour of a certain compound, or a salt of it, may be. This is typically only determined empirically.

In a further embodiment of the invention, there is provided a combination of the processes of the invention described herein. For example, there is provided a process for the preparation of a compound of formula I (which comprises reaction of a compound of formula II and III, as hereinbefore defined; referred to hereinafter as process (i)) followed by crystallisation (or precipitation) as hereinbefore described (referred to hereinafter as process (ii)). Preferably, process (ii) is performed directly after process (i), for example, by separation of the compound of formula I (e.g. by extraction and removal/evaporation of solvent), following by mixing/contacting the compound of formula I with the solvent system of the crystallisation process. Alternatively, in a further preferred embodiment of the invention, process (ii) can be performed directly after process (i) and in the same reaction pot.

Compounds of formula II and III may be known, or easily derived/synthesised from known compounds used standard steps or transformations known to those skilled in the art. However, in a further embodiment of the invention, there is provided a process for the preparation of a compound of formula II, as hereinbefore defined but in which $R^1$ represents H, which comprises reaction of a compound of formula IV,

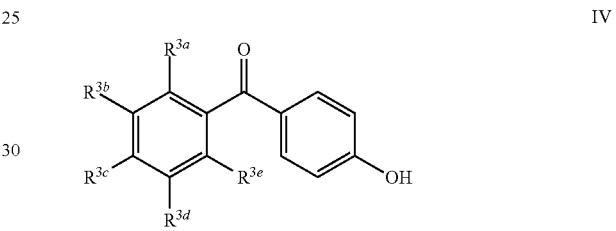

IV wherein $R^{3a}$ to $R^{3e}$ are as hereinbefore defined (and are preferably all H) with ethylene carbonate, in the presence of a catalyst, and characterised in that the reaction is carried out in the presence of less than 1 gram of solvent per gram of ethylene carbonate (or less than 1 gram of solvent per gram of compound of formula IV), which process is also referred to hereinafter as the process of the invention.

Alternatively, the compound of formula II may also be prepared by other standard reactions of a compound of formula IV as hereinbefore defined, with a compound of formula V, $$X^1\text{—}CH_2CH_2\text{—}OR^1 \qquad\qquad V$$

wherein $X^1$ represents a suitable leaving group, such as chloro, bromo, iodo or a sulfonate group, and $R^1$ is as hereinbefore defined, or a protected derivative thereof (e.g. an —OH protected derivative, when $R^1$ represents hydrogen), under standard alkylation reaction conditions, for example, in the presence of a base, such as an alkali metal based base (e.g. $Na_2CO_3$, $K_2CO_3$, $K_3PO_4$, t-BuONa, t-BuOK or, preferably, $CH_3ONa$), or mixtures of bases, and (a) suitable solvent(s) (such as dichloromethane, tetrahydrofuran, toluene, dimethylformamide or the like, or mixtures thereof) under standard conditions, such as at room temperature or elevated temperature (suitable reaction conditions may also be described in international patent application WO 01/60775).

The process of the invention (to obtain compounds of formula II) may be performed employing salts, solvates or protected derivatives of the starting compounds (of formula IV and ethylene carbonate). Compounds of formula II that may thereby be produced may or may not be produced in the form of a (e.g. corresponding) salt or solvate, or a protected derivative thereof.

Advantageously, in this process of the invention to obtain compounds of formula II, the product may be produced in very high yields, for example in greater than 80%, e.g. greater than 90%, or near quantitative yield. Further, the desired product may be isolated/purified by crystallisation.

It is stated herein that the process of the invention (for preparing a compound of formula II) may be performed in a certain quantity of solvent (or in the absence of solvent). When solvent is employed, then that solvent is preferably an aromatic solvent (e.g. benzene or, preferably, toluene or xylene or a mixture of xylenes, i.e. ortho-, meta- and/or para-xylene; the most preferred solvent is toluene). This process of the invention is performed in the presence of a relatively small volume/mass of solvent (or no solvent), i.e. at a high concentration. Preferably, it is performed in the presence of less than 1 gram of solvent per 5 g of compound of formula IV (more preferably, less than, or about, 1 gram per 10 g, particularly less than, or about, 1 gram per 20 g and, more particularly, less than, or about 1 gram per 25 g). Most preferably, the process of the reaction is performed in the presence of about 25 g of compound of formula IV per gram of solvent. Alternatively, the relatively high concentration of this process of the invention may be expressed in terms of moles of compound of formula IV per ml of solvent.

Hence, it may be performed in the presence of less than 100 ml of solvent per mole of compound of formula IV, for example, less than 50 ml per mole, preferably less than 25 ml per mole and, more preferably, less than 15 ml per mole. Most preferably, the process of the invention is performed in the presence of less than, or about 10 ml (e.g. about 9 ml) of solvent per mole of compound of formula IV.

In the process of the invention (for preparing a compound of formula II), it is stated above that a certain quantity of solvent may be employed. It is preferably the case that solvent is employed, for instance that ethylene carbonate may be dissolved in that solvent (in the quantities mentioned above) in order to avoid deposition of ethylene carbonate on a surface of the reaction vessel (for instance, when the surface is cold, this may occur). The amount of solvent may be important, for instance, it should not be excessive (otherwise the reaction vessel may need to be pressurised in order to reach certain reaction temperatures) but only a relatively small volume of solvent may be required, for example in comparison with ethylene carbonate, the amount of solvent may be less than 1 gram per 5 g of ethylene carbonate (more preferably, less than, or about, 1 gram per 10 g, particularly less than, or about, 1 gram per 15 g). The preferred solvents are mentioned above, the most preferred one being toluene.

The process of the invention (for preparing a compound of formula II) is performed in the presence of a catalyst, which may be any suitable catalyst, for instance a carbonate (such as potassium carbonate) or the like or, preferably, a metal halide, quaternary ammonium halide or quaternary phosphonium halide, or mixtures thereof. Such catalysts include sodium or potassium halide (where the halide may be chloride, bromide or iodide), tetraethylammonium halide (where the halide may be chloride, bromide or iodide), tetrabutylammonium halide (where the halide may be chloride, bromide or iodide), methyltrioctylammonium chloride and tetraethylphosphonium halide (where the halide may be chloride, bromide or iodide). Other catalysts include Group I or Group II (preferably Group I, i.e. the alkaline metals) halides (e.g. iodides, bromides and/or chlorides, especially lithium halides). Most preferred catalysts include metal (e.g. sodium) halides, especially sodium iodide. The quantity of catalyst is not germane to the process of the invention. However, it is preferred that a molar ratio of between 0.001:1 to 0.1:1 (e.g. 0.01:1 to 0.1:1) of catalyst:compound of formula IV is employed (e.g. a ratio of about 0.06:1 and most preferably about 0.03:1), but the skilled person will appreciate that more or less catalyst may be employed.

When the catalyst is a halide, the halide anions of the catalyst may first cause the ring opening of the ethylene carbonate, and together with loss of the proton of the hydroxy group (of the compound of formula IV) may form a carbonic acid mono-(2-chloroethyl) ester intermediate. The deprotonated hydroxy anion of the compound of formula IV may then react with any such intermediate form, which carbonic acid intermediate may undergo (e.g. concurrent) alkylation (e.g. in an nucleophilic substitution reaction, dispelling the halide) and decarboxylation, thereby forming the desired compound of formula II (and carbon dioxide and regenerating the halide anion).

The reagents/reactants employed in the process of the invention may be added at any stage and in any order, and the reaction mixture may be heated to a suitable temperature, e.g. to the reaction temperature that causes the reaction mixture to melt. For instance, the mixture of compound of formula IV, ethylene carbonate and solvent (which preferably boils at above 80° C., e.g. above 100° C.) may be heated to above room temperature, e.g. to above 60° C., such as above 80° C. (e.g. at about 88° C.; or any temperature that causes the mixture to melt) up to about 200° C. (depending on the solvent employed, more preferably, up to about 170° C., e.g. up to about 100° C.). The catalyst may then be added to this reaction mixture (although it may be added at any stage during the reaction; it may even be present from the start). The heating may be continued, for example until the reaction temperature is above 100° C., e.g. above 150° C. (e.g. between about 150° C. and 200° C., for instance about 170° C.). The reaction mixture may be allowed to react for a period of time that may be determined by the skilled person, in order to maximise yield.

After the process of the reaction (to prepare the compound of formula II), the mixture may be cooled (e.g. to below the operating temperature, which may be about 170° C.) for instance to below 150° C., e.g. below 125° C., and preferably to about 110° C.

The product of the process of the invention (e.g. of formula II) may be isolated and/or purified using any suitable method, for instance by flaking (cooling the melt), crystallisation (e.g. from toluene or the like, i.e. another suitable solvent) and/or by telescoping (after dilution by addition of solvent that may be employed in a subsequent step, e.g. in the process for preparing a compound of formula I; hence, 2-methyltetrahydrofuran may be employed).

The process of the invention (to prepare the compound of formula II) may be performed in the presence of, preferably, at least one equivalent of ethylene carbonate (in order to maximise yield) compared to the molar equivalents of compound of formula IV. However, up to 2 (e.g. up to about 1.5, e.g. up to about 1.2) equivalents of ethylene carbonate may be employed. A greater excess may also be employed, although this is not desired due to the additional unnecessary waste of unreacted starting material.

In a further embodiment of the invention, there is provided a combination of the processes of the invention described herein. For example, there is provided a process for the preparation of a compound of formula II (which comprises reaction of a compound of formula IV and ethylene carbonate, as hereinbefore defined; referred to hereinafter as process (iii)) followed by a process for the preparation of a compound of formula I (which comprises reaction of a compound of formula II and III; referred to hereinafter as process (i)), optionally followed by, crystallisation (or precipitation) as hereinbefore described (referred to hereinafter as process (ii)). That is, any of the processes described herein may advantageously be employed in conjunction (i.e. in sequence).

Furthermore, in a further embodiment of the invention, compounds of formula I in which $R^1$ represents hydrogen, which may be produced by the process of the invention described herein may further be modified, for example to produce compounds of formula I in which $R^1$ represents $C_{1-6}$ alkyl optionally substituted by one or more —OH groups. For instance, such compounds may be prepared by alkylation in the presence of a compound of formula VI,

$$X^2\text{—}R^{1a} \qquad\qquad VI$$

wherein $X^2$ represents a suitable leaving group, such as one hereinbefore defined in respect of $X^1$ (e.g. halo), and $R^{1a}$ represents $C_{1-6}$ alkyl optionally substituted by one or more —OH, under reaction conditions such as those described herein. Further, in the case, where compounds in which $R^1$ represents $C_{1-6}$ alkyl terminally substituted with a —OH group (e.g. —$CH_2$—$CH_2$—OH) are to be prepared, compounds of formula I in which $R^1$ represents H may be reacted with a compound of formula VII,

$$X^3\text{—}R^{1b}\text{—}C(O)OR^{1c} \qquad\qquad VII$$

wherein $X^3$ represents a suitable leaving group, such as one hereinbefore defined in respect of $X^1$ (e.g. halo), $R^{1b}$ represents $C_{1-5}$ alkyl, and $R^{1c}$ represents optionally substituted $C_{1-6}$ alkyl under standard alkylation reaction conditions such as those described herein, followed by appropriate reduction reaction conditions (e.g. those that promote the reduction of the ester moiety to a —$CH_2$—OH moiety, such as the presence of $LiAlH_4$, $LiBH_4$ or another suitable reducing agent). Such reaction conditions may be described in US patent application US 2008/0214860, the content of which is hereby incorporated by reference (in particular, the reaction conditions employed to promote the preparation of reactions of formula I in which $R^1$ represents —$CH_2$—$CH_2$—OH from corresponding compounds of formula I in which $R^1$ represents H).

Advantageously, and as stated herein, the processes employed herein may be sequentially combined, for instance, the following sequence may be mentioned: the process for preparing a compound of formula II (optional), followed by the process for preparing a compound of formula I in which $R^1$ represents H (which may employ a process for preparing a compound of formula II as described herein), followed by the conversion of that compound of formula I to one in which $R^1$ represents $C_{1-6}$ alkyl optionally substituted by one or more —OH (e.g. —$CH_2CH_2$—OH).

Intermediate compounds described herein, and derivatives thereof (e.g. protected derivatives), may be commercially available, are known in the literature or may be obtained by conventional synthetic procedures, in accordance with known techniques, from readily available starting materials using appropriate reagents and reaction conditions.

Substituents on compounds of formula I or any relevant intermediate compounds to such compounds (or salts, solvates or derivatives thereof), for instance substituents defined by $R^1$ and X, may be modified one or more times, before, after or during the processes described above by way of methods that are well known to those skilled in the art. Examples of such methods include substitutions, reductions, oxidations, alkylations, acylations, hydrolyses, esterifications, etherifications, halogenations, nitrations, diazotizations or combinations of such methods.

It is stated herein that specific functional groups may be protected. It will also be appreciated by those skilled in the art that, in the processes described above, other functional groups of intermediate compounds may be, or may need to be, protected by protecting groups.

In any event, functional groups which it is desirable to protect include hydroxy (although certain hydroxy groups in the processes described herein are specifically indicated as being unprotected, i.e. free —OH, derivatives). Suitable protecting groups for hydroxy include trialkylsilyl and diarylalkyl-silyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). However, most preferred protecting groups for hydroxy include alkylaryl groups, such as optionally substituted benzyl.

The protection and deprotection of functional groups may take place before or after any of the reaction steps described hereinbefore.

Protecting groups may be removed in accordance with techniques which are well known to those skilled in the art and as described hereinafter.

The use of protecting groups is described in "Protective Groups in Organic Chemistry", edited by J. W. F. McOmie, Plenum Press (1973), and "Protective Groups in Organic Synthesis", $3^{rd}$ edition, T. W. Greene & P. G. M. Wutz, Wiley-Interscience (1999).

The compounds of formula I obtained by the process of the invention may be separated and/or isolated by standard techniques, for instance by chromatography, crystallisation, evaporation of solvents and/or by filtration.

It should be appreciated that the purified compound of formula I so formed by the process of the invention may also contain materials other than those specified above.

This product may be further purified using any suitable separation/purification technique or combination of techniques including further crystallisation, distillation, phase separation, adsorption, e.g. using molecular sieves and/or activated carbon, and scrubbing.

The processes described herein may be operated as a batch process or operated as a continuous process. For instance, they may be conducted in 'flow-mode', and heated in any suitable way, e.g. by oil, steam, electricity or, preferably heated with microwaves (and hence the process may be performed using a continuous flow microwave-assisted organic synthesis apparatus) and may be conducted on any scale. Advantageously, using specific apparatus which is adapted to accommodate continuous flow microwave-assisted organic synthesis, then the reaction may be conducted on any scale (even on a relatively large scale) using microwave irradiation.

In general, the processes described herein, may have the advantage that the compounds of formula I may be produced in a manner that utilises fewer reagents and/or solvents, and/or requires fewer reaction steps (e.g. distinct/separate reaction steps) compared to processes disclosed in the prior art.

The processes of the invention may also have the advantage that the desired compounds (e.g. of formula I and/or formula II) is/are produced in higher yield, in higher purity, in higher selectivity (e.g. higher geometric selectivity), in less time, in a more convenient (i.e. easy to handle) form, from more convenient (i.e. easy to handle) precursors, at a lower cost and/or with less usage and/or wastage of materials (including reagents and solvents) compared to the procedures disclosed in the prior art. Furthermore, there may be several environmental benefits of the process of the invention, such as the circumvention of the use of certain solvents or reagents.

In further embodiments numbered 1-20 hereafter, the present invention includes

1. A process for the preparation of a compound of formula I,

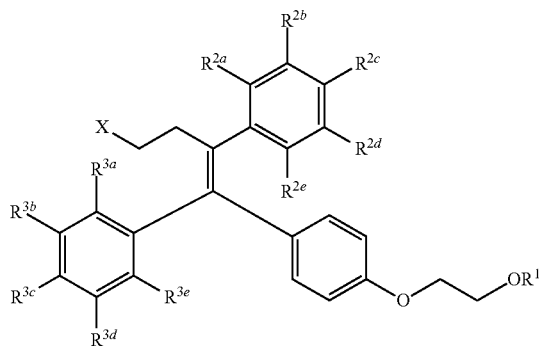

wherein:
X represents halo or —OH;
$R^1$ represents H or $C_{1-6}$ alkyl optionally substituted by one or more —OH group;
each $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ independently represent H or —OH;
which process comprises reaction of a compound of formula II,

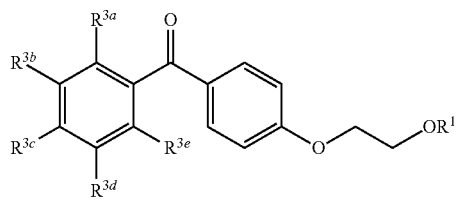

wherein $R^1$ and $R^{3a}$, $R^{3b}$, $R^{3c}$, $R^{3d}$ and $R^{3e}$ are as defined above, with a compound of formula III,

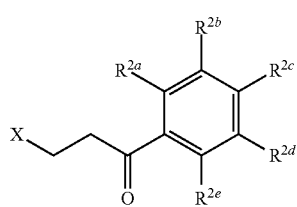

wherein X and $R^{2a}$, $R^{2b}$, $R^{2c}$, $R^{2d}$ and $R^{2e}$ are as defined above.

2. A process of embodiment 1, wherein X represents chloro.

3. A process of embodiments 1 or 2, wherein $R^1$ represents H, and/or $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ all represent H.

4. A process of any of embodiments 1 through 3, wherein the compound of formula I has a Z:E ratio of geometric isomers of greater than, or about, 4:1.

5. A process of any of embodiments 1 through 4, wherein the process is performed in the absence of solvent or in the presence of 2-methyltetrahydrofuran.

6. A process of any of embodiments 1 through 5, wherein the process is performed in the presence of a titanium chloride compound and a reducing agent.

7. A process of embodiment 6, wherein the titanium chloride compound and reducing agent are $TiCl_4$ and zinc (e.g. zinc dust).

8. A process of any of embodiments 1 through 7, wherein the molar ratio of the compounds of formula II and III in the process of the invention is about 1:1 and/or the molar equivalent of the titanium chloride compound (to compound of formula II or III) is about 1.3:1.

9. A process for the isolation/purification of a compound of formula I, as hereinbefore defined, which process comprises crystallisation or precipitation of the compound, in a solvent system, for instance, the process comprises crystallisation or precipitation of the compound of formula I obtained via a process of any of embodiments 1 through 8.

10. A process of embodiment 9, wherein the solvent system comprises an alcohol (e.g. methanol), optionally mixed with water.

11. A process of embodiments 9 or 10, wherein the compound of formula I is obtained in a Z:E ratio of greater than 10:1 and/or an HPLC purity of greater than 95%.

12. A process for the preparation of a compound of formula I (in which $R^1$ represents H) of any of embodiments 1 through 11, which first comprises preparation of a compound of formula II (as defined in embodiment 1 but in which $R^1$ represents H), which comprises reaction of a compound of formula IV,

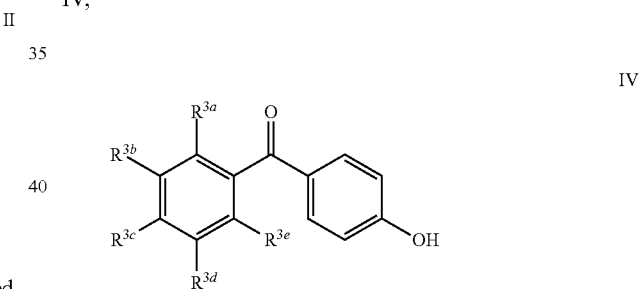

wherein $R^{3a}$ to $R^{3e}$ are as defined in embodiment 1 or 3, with ethylene carbonate, in the presence of a catalyst, and characterised in that the reaction is carried out in the presence of less than 1 gram of solvent per gram of ethylene carbonate.

13. A process of embodiment 12, which is performed in the presence of toluene or xylenes (e.g. where the solvent is present in an amount of less than 1 g per 5 g of ethylene carbonate).

14. A process of embodiment 12 or 13, wherein the catalyst is a carbonate, a metal halide, quaternary ammonium halide or quaternary phosphonium halide, or mixtures thereof.

15. A process of embodiment 14, wherein the catalyst is sodium or potassium iodide.

16. A process for the preparation of a compound of formula I as defined in any of any of embodiments 1 through 3, which process comprises:
(i) a process for the preparation of a compound of formula II of any of embodiments 12 to 15;
(ii) a process for the preparation of a compound of formula I of any of embodiments 1 through 8, wherein the compound of formula II is obtained from process step (i) described above; and, optionally, (iii) isolation of the compound of formula I obtained by step (ii) above according to a process of any of embodiments 9 through 11.

17. A process for the preparation of a compound of formula I of embodiment 1 but in which $R^1$ represents $C_{1-6}$ alkyl terminally substituted with a —OH group (e.g. —CH$_2$—CH$_2$—OH), which comprises preparation of a compound of formula I in which $R^1$ represents H (of any of embodiments 1 through 11) followed by reaction with a compound of formula VII,

wherein $X^3$ represents a suitable leaving group, $R^{1b}$ represents $C_{1-5}$ alkyl (e.g. —CH$_2$—), and $R^{1c}$ represents optionally substituted $C_{1-6}$ alkyl, followed by reduction (of the ester moiety to a —CH$_2$—OH moiety).

18. A process for preparing a pharmaceutical formulation comprising a compound of formula I, or a salt thereof, which process is characterised in that it includes as a process step a process of any of embodiments 1 through 13 or 17 (e.g. embodiments 1 to 10, 16 or 17).

19. A process for the preparation of a pharmaceutical formulation comprising a compound of formula I, or a salt thereof, which process comprises a process for the preparation of a compound of formula I, or, a salt thereof, of any of embodiments 1 through 13 or 17 (e.g. embodiments 1 to 10, 16 or 16), followed by bringing into association the compound of formula I (or a salt thereof) so formed, with (a) pharmaceutically-acceptable excipient(s), adjuvant(s), diluent(s) or carrier(s).

20. A process or compound substantially as described herein with reference to the following examples.

The following examples are merely illustrative examples of the processes of the invention described herein.

All equipment, reagents and solvents used were standard laboratory equipment, e.g. glassware, heating apparatus and HPLC apparatus.

EXAMPLE 1A (A) Synthesis of 4-(2-hydroxyethoxy)benzophenone (i) A mixture of ethylene carbonate (14.26 g), xylenes (1.19 g) and 4-hydroxybenzophenone (30.41 g) was heated to 88° C. Sodium iodide (1615 mg) was added. Heating was continued until the temperature of the mixture reached 169° C. The melt was cooled to 110° C. and methanol (12.76 g), sodium hydroxide (50% aqueous solution; 4.01 g), toluene (42.51 g) and water (28.88 g) were added. The lower layer was separated ('cut') and discarded. Toluene (18.1 g) was added and the solvents were evaporated by heating to the boiling point of 111° C. 4-(2-Hydroxyethoxy)benzophenone was isolated by crystallisation and filtration at 17° C. resulted in 34.1 g (92%) of beige crystals.

(ii) A mixture of ethylene carbonate (124.6 g; 1.07 eq.), sodium iodide (6.3 g; 0.03 eq.), 4-hydroxybenzophenone (262 g; 1 eq.) and toluene (8.1 g) was heated. At 99° C. a clear solution was obtained. The reaction mixture was heated with reflux condenser to 176° C. over one hour, during which gas evolution occurred. After an additional ½ hour at 176° C., the reaction mixture was cooled to 122° C. and toluene (350 g) and water (24 g) was added. The lower phase was cut and discarded. More water (14 g) was added and the lower phase was again cut and discarded. Water and toluene (95 g in total) was azeotropically removed, reaching a boiling point of 111° C. More toluene (114 g) was added and the product was isolated by filtration at 8° C. In total, 302 g of 4-(2-hydroxyethoxy)benzophenone (94%) was obtained after drying as white crystals (99.8% chromatographic purity).

(B) Synthesis of Ospemifene®

Nitrogen atmosphere was applied during the reaction. Zinc dust (1.29 g; 19.76 mmol; 2.66 equiv.) and 2-methyl-THF (14 mL) were charged to a flask and cooled to below −5° C. TiCl$_4$ (1.1 mL; 10.03 mmol; 1.35 equiv.) was slowly added (over 20 minutes; as the addition is exothermic) to the zinc-slurry, maintaining the temperature below 0° C. The reaction mixture was heated to reflux (82° C.) and refluxed for 2 hrs. A prepared solution of both ketones (1.80 g of 4-(2-hydroxyethoxy)benzophenone (see (A) above); 7.43 mmol; 1 equiv.; 1.25 g of 3-chloropropiophenone; 7.43 mmol; 1 equiv) in 2-methyl-THF (5 mL) was slowly added to the black reaction mixture at reflux. The temperature rose to 85° C. The reaction mixture was refluxed for 2 hours. The reaction mixture was then cooled to room temperature. 4.6 mL of 1M HCl and 4.2 mL of 6 M HCl were added and the mixture stirred for 10 minutes. Then 13 mL toluene was added and the reaction mixture was stirred for 15 min. The layers were separated. The toluene layer was washed with 4 mL water and dried over MgSO$_4$. Quantitative HPLC from toluene solution shows 38% yield and the ratio of Z/E isomers of Ospemifene 4.3/1. The toluene solution was washed with 8.5 mL conc. NaHCO$_3$, 6 mL water and dried over MgSO$_4$. 3.05 g of crude product was obtained after concentration on a rotavapor (bath 34° C.). Crystallization in methanol (13 mL) and water (2.5 mL) gave an oil. This solution was heated until it was a clear solution and then let to cool slowly to room temperature (crystals appeared) and then left to stand overnight at +8° C. The crystals were filtered, rinsed with 60% MeOH/water and dried. 0.787 g of light yellow solid was obtained, at 92.8% purity by HPLC (area %), and a yield of 26% (calculated as pure product).

(C) Synthesis of Fispemifene (i) Fispemifene® is prepared directly from the McMurry reaction of 3-chloropropionphenone with the appropriate benzophenone.

(ii) Fispemifene® is also prepared by reaction of Ospemifene® (produced by (B) above) by reaction in the presence of a compound of formula VII as herein defined but in which $R^{1b}$ represents —CH$_2$—, followed by reduction of the intermediate so formed.

EXAMPLE 1B

Alternative Synthesis of Ospemifene

Hydroxyethoxybenzophenone (67.66 g, 279.3 mmol, 1 eq), 3-chloropropiophenone (47.24 g, 279.3 mmol, 1 eq), zinc powder (69.45 g, 1062 mmol, 3.8 eq) and 2-methyltetrahydrofuran (895 g, 1041 ml) were charged to the reactor. The slurry was degassed and the vessel was filled with nitrogen gas. The slurry was cooled to <15° C. and then titanium tetrachloride (101.5 g, 535.1 mmol, 1.92 eq.) was slowly dosed maintaining a temperature below 20° C. The slurry was heated to 50° C. and the temperature was maintained for 15 minutes. The slurry was heated to 70° C. and the pressure was reduced and 2-methyltetrahydrofuran (403 g) was distilled off at 70° C. and 650 mbar over 1 hour. Zinc(s) was filtered off and the filter was rinsed with 2-methyltetrahydrofuran (64 g). The pressure was reduced to 200 mbar and 2-methyltetrahydrofuran (344 g) was distilled off at 43-53° C. and 200-160 mbar pressure (total amount of pure 2-methyltetrahydrofuran recycled is 76%). Toluene (151 g) was charged. A mixture of hydrochloric acid (aq) (116 g, 37%) and water (281 g) was added maintaining a temperature below 20° C. The lower aqueous phase was cut (at 30° C.) and discarded. Water (128 g) was added. The lower aqueous phase was cut (at 55° C.) and discarded. Water (131 g) was added again and the lower aqueous phase was cut again (at 55° C.) and discarded. The pressure was reduced and 2-methyltetrahydrofuran+toluene+water was distilled off at 150-50 bar and 37-60° c. until there was a residual volume of about 130 ml. Before the crystallisation/precipitation process, the ratio of Z:E isomers of Ospemifene was about 5.5:1. Then, methanol (125 g) was charged and the solution was filtered. To the filtrate was added methanol to a total weight of 572 g (content estimated to 121 g raw product+toluene and 451 g methanol). Water (148 g) was added to the filtrate and the solution was heated to 50° C. The solution was then cooled to 48° C. and seeded. The mixture was slowly cooled to 15° C. over 5 hours and maintained at this temperature overnight. The product was isolated by filtration and the filter cake was rinsed with methanol(aq) (74%, 141 g). Yield 50.4 g after drying (47.6%). Purity>99% by HPLC (standard). The raw product contained 98.81% Z-isomer, 0.61% E-isomer (hence a ZE ratio of 162:1) and 0.58% of other products. The product obtained (in a yield of 96%; hence, advantageously yield is not significantly decreased) after recrystallisation was 99.9% Z-isomer, 0.05% E-isomer (hence a Z:E ratio of 1991:1) and 0.05% of other products.

Hence, an extremely pure and selective Z-isomer of the compound of formula I is obtained by this method of the invention.

EXAMPLE 2

Ospemifene®, or another suitable compound of the invention (e.g. Fispemifene®), may be formulated into a pharmaceutically acceptable formulation using standard procedures.

For example, there is provided a process for preparing a pharmaceutical formulation comprising Ospemifene® (or another suitable compound of the invention, e.g. Fispemifene®), or a salt thereof, which process is characterised in that it includes as a process step a process as hereinbefore defined. The skilled person will know what such pharmaceutical formulations will comprise/consist of (e.g. a mixture of active ingredient (i.e. Ospemifene®, or another suitable compound of the invention, e.g. Fispemifene®, or a salt thereof) and pharmaceutically acceptable excipient, adjuvant, diluent and/or carrier).

There is further provided a process for the preparation of a pharmaceutical formulation comprising Ospemifene® (or another suitable compound of the invention, e.g. Fispemifene®; or a salt thereof), which process comprises bringing into association Ospemifene® (or another suitable compound of the invention, e.g. Fispemifene®), or a pharmaceutically acceptable salt thereof (which may be formed by a process as hereinbefore described), with (a) pharmaceutically acceptable excipient(s), adjuvant(s), diluent(s) and/or carrier(s).

The invention claimed is:

1. A process for the preparation of a compound of formula I,

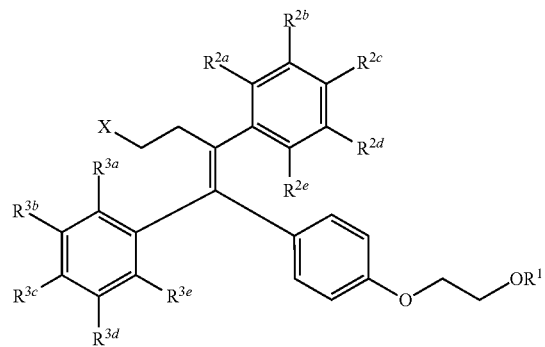

wherein:
X represents halo or —OH;
$R^1$ represents H or $C_{1-6}$ alkyl optionally substituted by one or more —OH group;
each $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ independently represent H or —OH;
which process comprises reaction of a compound of formula II,

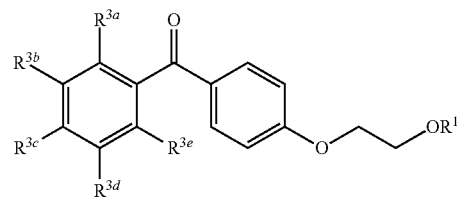

wherein $R^1$ and $R^{3a}$, $R^{3b}$, $R^{3c}$, $R^{3d}$ and $R^{3e}$ are as defined above, with a compound of formula III,

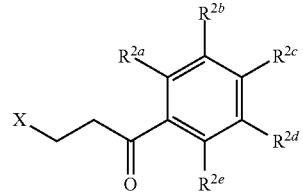

wherein X and $R^{2a}$, $R^{2b}$, $R^{2c}$, $R^{2d}$ and $R^{2e}$ are as defined above.

2. The process of claim 1, wherein X represents chloro.

3. The process of claim 1, wherein $R^1$ represents H, and $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ all represent H.

4. The process of claim 1, wherein the compound of formula I has a Z:E ratio of geometric isomers of greater than, or about, 4:1.

5. The process of claim 1, wherein the process is performed in the absence of solvent or in the presence of 2-methyltetrahydrofuran.

6. The process of claim 1, wherein the process is performed in the presence of a titanium chloride compound and a reducing agent.

7. The process of claim 6, wherein the titanium chloride compound is TiCl$_4$ and the reducing agent is zinc.

8. The process of claim 1, wherein the molar ratio of the compounds of formula II and III is about 1:1.

9. A process for the isolation/purification of a compound of formula

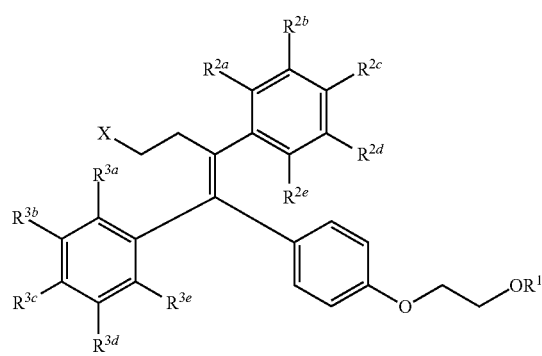

wherein:
X represents halo or —OH;
R$^1$ represents H or C$_{1-6}$ alkyl optionally substituted by one or more —OH group;
each R$^{2a}$, R$^{2b}$, R$^{2c}$, R$^{2d}$, R$^{2e}$, R$^{3a}$, R$^{3b}$, R$^{3c}$, R$^{3d}$ and R$^{3e}$ independently represent H or —OH;
which process comprises preparing a compound of formula I by the process of claim 1, followed by crystallization or precipitation of the compound, in a solvent system.

10. The process of claim 9, wherein the solvent system comprises an alcohol optionally mixed with water.

11. The process of claim 9, wherein the compound of formula I is obtained in a Z:E ratio of greater than 10:1.

12. A process for the preparation of a compound of formula I

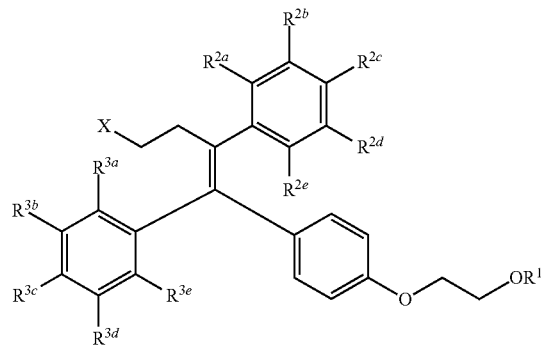

wherein:
X represents halo or —OH;
R$^1$ represents H;
each R$^{2a}$, R$^{2b}$, R$^{2c}$, R$^{2d}$, R$^{2e}$, R$^{3a}$, R$^{3b}$, R$^{3c}$, R$^{3d}$ and R$^{3e}$ independently represent H or —OH, which first comprises preparation of a compound of formula II

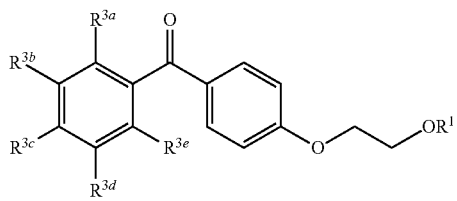

wherein R$^1$ and R$^{3a}$, R$^{3b}$, R$^{3c}$, R$^{3d}$ and R$^{3e}$ are as defined above, by reaction of a compound of formula IV,

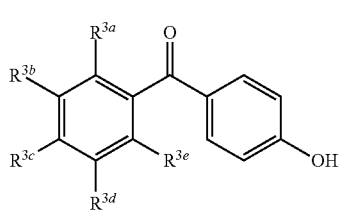

wherein R$^{3a}$ to R$^{3e}$ are as defined above, with ethylene carbonate, in the presence of a catalyst, and characterised in that the reaction is carried out in the presence of less than 1 gram of solvent per gram of ethylene carbonate, followed by reaction of the compound of formula II with a compound of formula III,

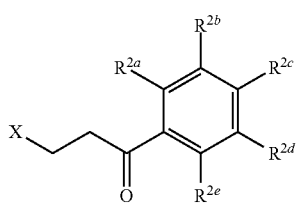

wherein X and R$^{2a}$, R$^{2b}$, R$^{2c}$, R$^{2d}$ and R$^{2e}$ are as defined above.

13. The process of claim 12, which is performed in the presence of toluene or xylenes as a solvent and wherein the solvent is present in an amount of less than 1 g per 5 g of ethylene carbonate.

14. The process of claim 12, wherein the catalyst is a carbonate, a metal halide, quaternary ammonium halide or quaternary phosphonium halide, or mixtures thereof.

15. The process of claim 14, wherein the catalyst is sodium or potassium iodide.

16. A process for the preparation of a compound of formula I

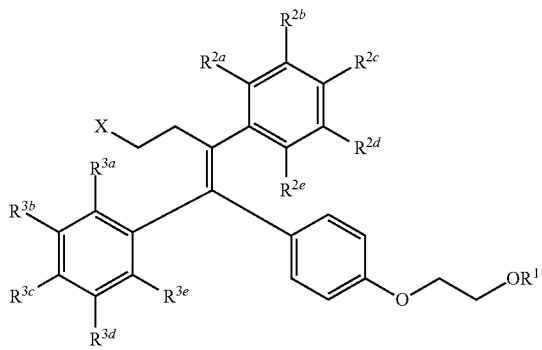

wherein:
X represents halo or —OH;
$R^1$ represents $C_{1-6}$ alkyl terminally substituted with a —OH group, each $R^{2a}$, $R^{2b}$, $R^{2c}$, $R^{2d}$, $R^{2e}$, $R^{3a}$, $R^{3b}$, $R^{3c}$, $R^{3d}$ and $R^{3e}$ independently represent H or —OH;
which comprises preparation of a compound of formula I in which $R^1$ represents H by reaction of a compound of formula II,

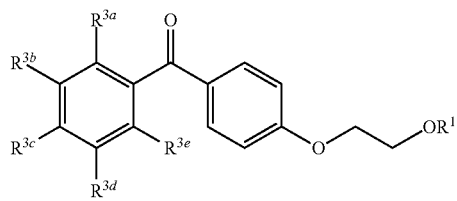

wherein $R^1$ is hydrogen and $R^{3a}$, $R^{3b}$, $R^{3c}$, $R^{3d}$ and $R^{3e}$ are as defined above, with a compound of formula III,

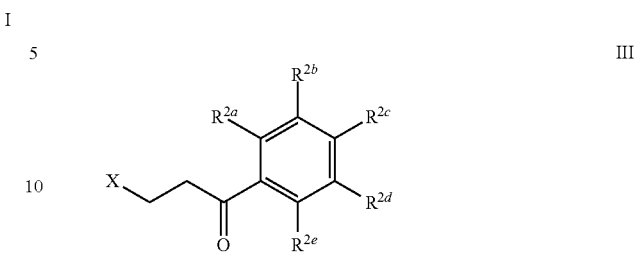

wherein X and $R^{2a}$, $R^{2b}$, $R^{2c}$, $R^{2d}$ and $R^{2e}$ are as defined above followed by reaction with a compound of formula VII,

wherein $X^3$ represents a suitable leaving group, $R^{1b}$ represents $C_{1-5}$ alkyl and $R^{1c}$ represents optionally substituted $C_{1-6}$ alkyl, followed by reduction.

17. The process of claim 7 wherein the zinc is zinc dust.

18. The process of claim 6 wherein the molar equivalent of the titanium chloride compound (to compound of formula II or III) is about 1.3:1.

19. The process of claim 6 wherein the molar ratio of the compounds of formula II and III is about 1:1 and the molar equivalent of the titanium chloride compound (to compound of formula II or III) is about 1.3:1.

20. The process of claim 10 wherein the alcohol is methanol.

21. The process of claim 9, wherein the compound of formula I is obtained in an HPLC purity of greater than 95%.

* * * * *